(12) United States Patent
Tissandier

(10) Patent No.: US 8,240,201 B2
(45) Date of Patent: Aug. 14, 2012

(54) AIR MONITORING DEVICE

(75) Inventor: Michael D. Tissandier, Alto Loma, CA (US)

(73) Assignee: Hamilton Sundstrand Space Systems International, Inc., Windsor Locks, CT (US)

( * ) Notice: Subject to any disclaimer, the term of this patent is extended or adjusted under 35 U.S.C. 154(b) by 140 days.

(21) Appl. No.: 12/709,739

(22) Filed: Feb. 22, 2010

(65) Prior Publication Data

US 2011/0203363 A1 Aug. 25, 2011

(51) Int. Cl.
*G01W 1/00* (2006.01)
(52) U.S. Cl. .................................................. 73/170.01
(58) Field of Classification Search ................. None
See application file for complete search history.

(56) References Cited

U.S. PATENT DOCUMENTS

| | | | |
|---|---|---|---|
| 4,670,135 A | 6/1987 | Marple et al. | |
| 5,425,802 A * | 6/1995 | Burton et al. | 95/32 |
| 5,788,741 A * | 8/1998 | Burton et al. | 95/32 |
| 6,062,392 A | 5/2000 | Birmingham et al. | |
| 6,698,592 B2 | 3/2004 | Kenning et al. | |
| 2007/0240520 A1* | 10/2007 | Kim et al. | 73/861.71 |
| 2008/0028869 A1* | 2/2008 | Kim et al. | 73/861.71 |

OTHER PUBLICATIONS

Hinds, Aerosol Technology Properties, Behavior, and Measurement of Airborne Particles, 1999, pp. 134-136, second edition, John Wiley & Sons, Inc., Los Angeles, California.

* cited by examiner

*Primary Examiner* — Andre Allen
(74) *Attorney, Agent, or Firm* — Cantor Colburn LLP

(57) ABSTRACT

An air monitoring device (100) includes an outer casing (101) configured to receive an airflow (102) comprising particulate; a bore (103) located inside the outer casing (101); and a collection probe (104) located inside the outer casing (101), the collection probe (104) being configured such that there is a gap (105) between an exit of the bore (103) and an entrance of the collection probe (104), such that particulate in the airflow (102) having a diameter larger than a threshold flows through an interior of the collection probe (104).

7 Claims, 1 Drawing Sheet

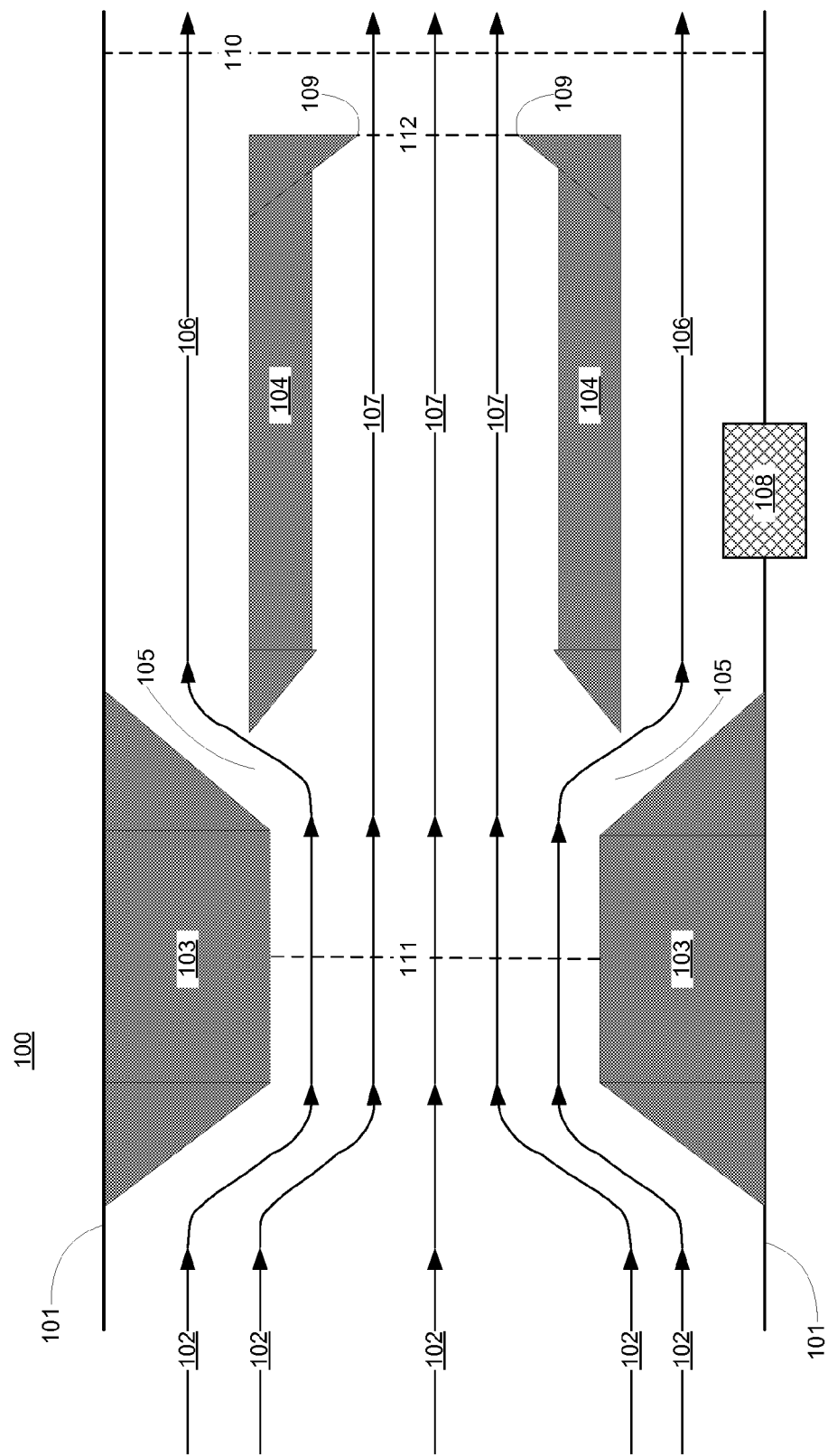

AIR MONITORING DEVICE

FEDERAL RESEARCH STATEMENT

This invention was made with Government support under Government Contract NNJ06TA25C, awarded by the National Aeronautics and Space Administration (NASA). The Government has certain rights in this invention.

FIELD OF INVENTION

The subject matter disclosed herein generally relates to the field of air monitoring.

DESCRIPTION OF RELATED ART

The separation of particulate matter from gas is necessary for various air monitoring applications, including atmospheric analysis of the gas, characterization of particulates in the gas, and for protecting mechanical or electronic equipment from the particulates in the gas. In some air monitoring applications, the gas is sampled at an interface between the gas located outside the monitoring device, which is at atmospheric pressure, and a vacuum located inside the monitoring device. The interface may comprise a frit comprising sintered metal configured to have a series of micron-sized pores. The pores may become blocked if particulate having a diameter greater than or equal to the pore size is allowed to impinge on the surface of the frit.

A virtual impactor is a type of air monitoring device that addresses frit clogging by separating large particulate and the gas being monitored into two separate airflows for sampling. However, the two flow paths in a virtual impactor device require separate pumps and separate flow control devices, which may increase the size, weight, power drain, and complexity of the air monitoring device.

BRIEF SUMMARY

According to one aspect of the invention, an air monitoring device includes an outer casing configured to receive an airflow comprising particulate; a bore located inside the outer casing; and a collection probe located inside the outer casing, the collection probe being configured such that there is a gap between an exit of the bore and an entrance of the collection probe, such that particulate in the airflow having a diameter larger than a threshold flows through an interior of the collection probe.

Other aspects, features, and techniques of the invention will become more apparent from the following description taken in conjunction with the drawings.

BRIEF DESCRIPTION OF THE SEVERAL VIEWS OF THE DRAWINGS

Referring now to the drawings wherein like elements are numbered alike in the several FIGURES:

FIG. 1 illustrates a cross-section of an embodiment of an air monitoring device.

DETAILED DESCRIPTION

Embodiments of an air monitoring device are provided, with exemplary embodiments being discussed below in detail.

A cross-section of an embodiment of an air monitoring device is shown in FIG. 1. Air monitoring device 100 comprises an outer casing 101 containing a bore 103 and a collection probe 104; outer casing 101, bore 103, and collection probe 104 may be cylindrical in some embodiments. A gap 105 is located between the exit of the bore 103 and the entrance to collection probe 104. Particulate-filled airflow 102 enters the outer casing 101 and is accelerated through bore 103. The bore 103 has a diameter (indicated by dashed line 111) that is smaller than a diameter (indicated by dashed line 110) of the outer casing 101; therefore, bore 103 acts to accelerate airflow 102. Bore 103 is sufficiently long to ensure the particles in airflow 102 reach a relatively high velocity, and therefore have a large momentum. As the airflow 102 exits the bore 103, airflow 102 splits into airflow 106 and airflow 107 (airflow 106 and 107 are also referred to as portion 106 and 107 of airflow 102). Particles in airflow 102 having a diameter larger than a particle size threshold become part of airflow 107. Due to the large momentum imparted by the acceleration of airflow 102 in bore 103, the particles larger than the threshold in airflow 102 are unable to make the turn through the gap 105, and enter the collection probe 103 as part of airflow 107. Airflow 107 may also comprise particles having a diameter smaller than or equal to the particle threshold. Airflow 106 comprises only particles having a diameter smaller than or equal to the particle threshold. The particles smaller than the threshold in airflow 106 have relatively low momentum, and may successfully turn through gap 105 and flow between the exterior of collection probe 104 and the interior of outer casing 101. Airflow 106 interacts with frit 108 for sampling and analysis. Because airflow 106 only contains particulate having a diameter smaller than or equal to the threshold size, airflow 106 may be sampled without clogging the frit 108. Frit 108 may be located in any appropriate location in the outer diameter of outer casing 101 in between the gap 105 and the end of collection probe 104, and may be relatively close to the gap 105 in some embodiments. Airflows 106 and 107 exit the outer casing 101 after passing around (in the case of airflow 106) or through (in the case of airflow 107) collection probe 104. Bore 103 and collection probe 104 may be relatively simple to produce, and require no active control once appropriate airflow is established through air monitoring device 100.

The particle threshold may be a particle diameter of about 0.2 microns in some embodiments; the particle threshold may be made larger or smaller by adjusting the ratio of the flow velocities between the outside and inside of the collection probe 104. The ratio of flow velocities may be adjusted by adjusting the diameter (indicated by dashed line 112) of the necking 109, the size of the gap 105, the flow rate of airflow 102, and/or the diameter 111 of bore 103 (which determines amount of acceleration imparted to airflow 102 in bore 103). However, there are physical limits on the range of flow velocities that may be attained, which also act to limit the particle threshold at relatively small sizes. As the particle threshold approaches smaller and smaller sizes, the gap 105 between the collection probe 104 and the bore 103 must become smaller. This decreases the conductance through the gap 105, and thus, airflow 106 to the frit 108, to the point that none of airflow 102 may flow through gap 105. In this case, frit 108 may only measure air trapped outside the collection probe 104. This may be mitigated by reducing the diameter 112 of the necking 108; however, this has the effect of restricting total airflow through the air monitoring device 100.

The technical effects and benefits of exemplary embodiments include a relatively small, lightweight air monitor that prevents clogging of the sampling frit.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. Many modifications, variations, alterations, substitutions, or equivalent arrangement not hereto described will be apparent to those of ordinary skill in the art without departing from the scope and spirit of the invention. Additionally, while various embodiment of the invention have been described, it is to be understood that aspects of the invention may include only some of the described embodiments. Accordingly, the invention is not to be seen as limited by the foregoing description, but is only limited by the scope of the appended claims.

The invention claimed is:

1. An air monitoring device (100), comprising:
    an outer casing (101) configured to receive an airflow (102) comprising particulate;
    a bore (103) located inside the outer casing (101);
    a collection probe (104) located inside the outer casing (101), the collection probe (104) being configured such that there is a gap (105) between an exit of the bore (103) and an entrance of the collection probe (104), such that particulate in the airflow (102) having a diameter larger than a threshold flows through an interior of the collection probe (104), wherein a portion (106) of the airflow (102) comprising particulate having a diameter smaller than or equal to the threshold flows through the gap (105) and between an exterior of the collection probe (104) and an interior of the outer casing (101); and
    a frit (108) located on the outer casing (101) between the gap (105) and an exit of collection probe (104), the frit (108) configured to sample the portion (106) of the airflow (102) comprising particulate having a diameter smaller or equal to than the threshold.

2. The air monitoring device (100) of claim 1, wherein the collection probe (104) comprises necking (109) at an exit of the collection probe (104), the necking (109) having a diameter (112), and wherein the threshold is determined based on the diameter (112) of the necking (109).

3. The air monitoring device (100) of claim 1, wherein the threshold is determined based on a flow rate of the airflow (102).

4. The air monitoring device (100) of claim 1, wherein the threshold is about 0.2 microns.

5. The air monitoring device (100) of claim 1, wherein the bore (103) has a diameter (111) that is smaller than a diameter (110) of the outer casing (101), and wherein the bore (103) is configured to increase a velocity of the airflow (102).

6. The air monitoring device (100) of claim 5, wherein the threshold is determined based on the diameter (111) of the bore (103).

7. The air monitoring device (100) of claim 1, wherein the threshold is determined based on a size of the gap (105).

* * * * *